United States Patent

Naizer et al.

[11] 4,072,043
[45] Feb. 7, 1978

[54] METHOD AND SYSTEM FOR DETECTING HYDROGEN IN AN INERT GAS STREAM

[75] Inventors: Kenneth C. Naizer, Nederland; Jesse K. DuBose, Beaumont, both of Tex.

[73] Assignee: Texaco Inc., New York, N.Y.

[21] Appl. No.: 752,048

[22] Filed: Dec. 20, 1976

[51] Int. Cl.² ............................................. G01N 31/00
[52] U.S. Cl. ......................................................... 73/23
[58] Field of Search .......................... 73/19, 23, 27 R; 340/237 R; 23/232 R, 232 E, 254 R, 254 E

[56] References Cited

U.S. PATENT DOCUMENTS

| | | | |
|---|---|---|---|
| 2,010,995 | 8/1935 | Jacobson | 73/27 R |
| 3,010,801 | 11/1961 | Schulze | 23/232 R |
| 3,153,577 | 10/1964 | McCully et al. | 73/27 R |
| 3,279,241 | 10/1966 | Pement | 73/23 |
| 3,976,450 | 8/1976 | Marcote et al. | 73/23 |

Primary Examiner—Richard C. Queisser
Assistant Examiner—Stephen A. Kreitman
Attorney, Agent, or Firm—Thomas H. Whaley; Carl G. Ries; Henry C. Dearborn

[57] ABSTRACT

A mixing chamber and system for connecting it to a stream of inert gas, in order to monitor the stream for detecting the presence of hydrogen therein. It has a hydrogen detector in the chamber, and there is a stream of dry air mixed with the inert gas stream to provide oxygen which is required for operation of the hydrogen detector.

5 Claims, 3 Drawing Figures

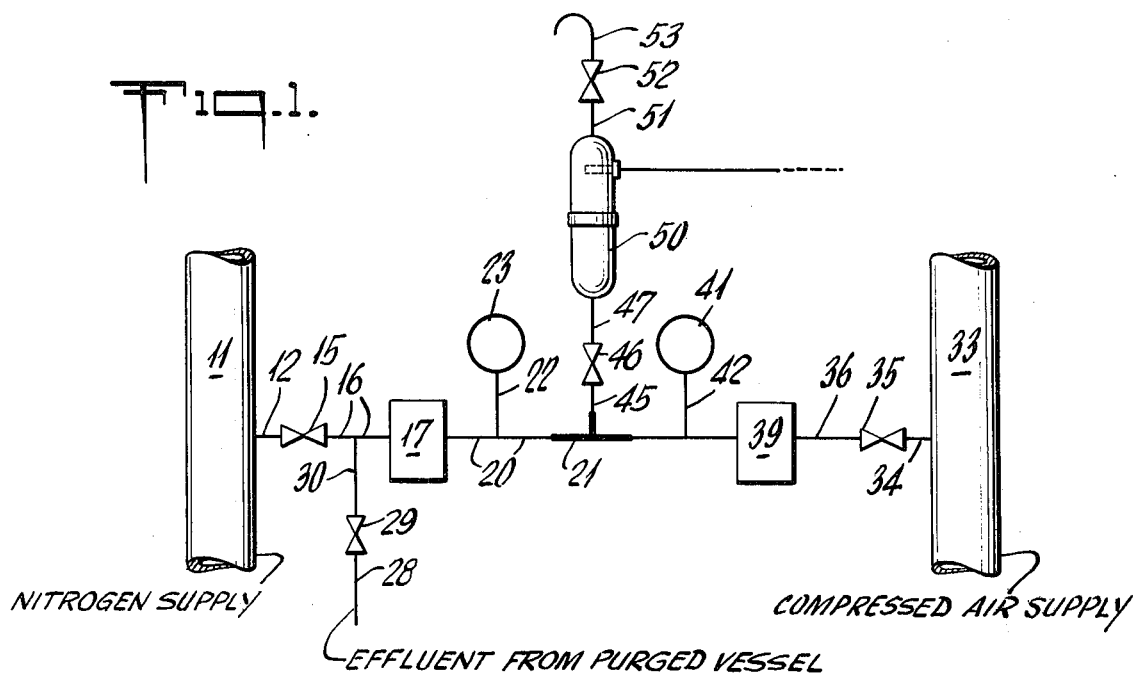
Fig. 1.
NITROGEN SUPPLY
EFFLUENT FROM PURGED VESSEL
COMPRESSED AIR SUPPLY
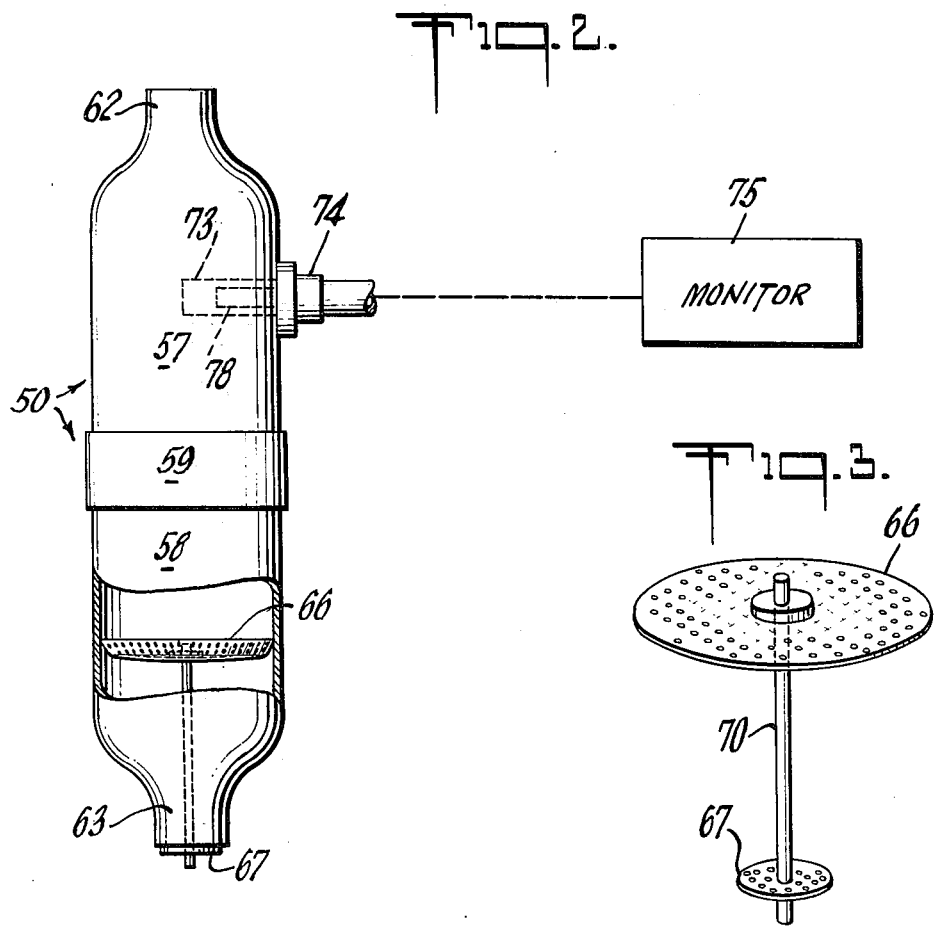
Fig. 2.
MONITOR
Fig. 3.

4,072,043

METHOD AND SYSTEM FOR DETECTING HYDROGEN IN AN INERT GAS STREAM

BACKGROUND OF THE INVENTION

1. Field of the Invention

This invention concerns the detection of hydrogen in an inert gas stream. More specifically, it concerns a method and system for detecting hydrogen in an inert gas stream which stream includes dry air for providing an oxidizing component. It also particularly relates to apparatus that is applicable to a system for continuously monitoring an inert gas stream, in order to detect any hydrogen which may be included therein.

2. Description of the Prior Art

In operations where large vessels, or the like, are filled with an inert gas in order to provide a working atmosphere therein which is needed for maintenance operations such as welding or cutting or the like within such vessels, it has been found that there are possible dangerous conditions developed. Such dangerous conditions are due to pockets or small areas within the entire space, which may go undetected by the known prior methods of determining the safety of such atmosphere.

Thus, it has been a past procedure to introduce a supply of nitrogen gas into a vessel that is to be worked upon by personnel on the interior thereof. Such work involved the use of cutting, burning or welding operations such that any explosive atmosphere encountered would be detonated and thus jeopardize the personnel. The past practice was to fill such vessel with a supply of nitrogen, and then to test the safety of the atmosphere in the vessel by using a hand held detection device. A serious question of safety was inherent in that procedure since any hydrogen which may have existed in the pure form or as a hydrocarbon or the like, would tend to form into or gather as pockets with considerable concentration. Such pockets might readily go undetected by the indicated prior procedure, but because of convection currents or the like they could easily be detonated.

Consequently, it is an object of this invention to provide a method and system for eliminating the possible dangers inherent in past procedures which were used for inerting the atmosphere in large size vessels.

Another object of the invention is to provide a system which includes structure for continous monitoring of a gas stream in such a manner that the atmosphere of a vessel to be inerted may be continously monitored as its neutralizing is taking place. The system includes as an element thereof a particular monitoring chamber structure with related elements, such that the sample gas stream will pass therethrough and may be continously monitored for the presence of hydrogen therein.

SUMMARY OF THE INVENTION

Briefly, the invention relates to a system for monitoring an inert gas stream in order to detect hydrogen therein. It comprises in combination a chamber for passing at least a portion of said gas stream therethrough. It has an inlet and an outlet. The combination also comprises means associated with said inlet for diffusing mixed gas streams and for collecting any moisture therefrom, and means for mounting a hydrogen detector in said chamber down stream from said diffusing means. It also comprises means for preventing moisture from entering said outlet.

Again briefly, the invention concerns a method for detecting the presence of hydrogen in a stream of inert gas which comprises mixing a stream of air with said inert gas stream, and filtering both said streams to remove moisture therefrom. It also comprises diffusing said mixed streams of inert gas and air at the entrance of a detection chamber, and monitoring said diffused streams in said detection chamber for detecting any hydrogen therein. It also comprises flowing said diffused streams out of said chamber while preventing any moisture from entering therein.

Once more briefly, the invention concerns an adaptor for inline hydrogen detection which comprises in combination an elongated cylindrical chamber that in turn comprises two pressed metal portions joinded by a collar. Each of the said portions has a necked down end, and one of said ends forms an inlet while the other forms an outlet of said chamber. The adaptor also comprises means for diffusing an incoming gas at said inlet. The diffusing means, in turn, comprises a pair of perforated thin discs attached to an axial spacer rod and extending transversely thereof. One of said discs has a diameter slightly greater than the inside diameter of said pressed metal portions. The other of said discs has a diameter slightly greater than the inside diameter of said inlet, and said discs and spacer rod are adapted for mounting in said inlet portion of said chamber prior to joinder of said outlet portion with said collar. The adaptor also comprises a hole in the side of said outlet portion of said chamber, adapted for mounting a hydrogen detector transversely in said chamber, and means associated with said outlet for preventing entry of water therethrough. The last name means comprises a vent pipe connected to said outlet having a valve connected therein for shutting said vent when the adaptor is not being used for hydrogen detection. The said vent pipe ends in a half circle curve downward when the adaptor is in use, in order to keep said water out.

BRIEF DESCRIPTION OF THE DRAWINGS

The foregoing and other objects and benefits of the invention will be more fully set forth below in connection with the best mode contemplated by the inventors of carrying out the invention and in connection with which there are illustrations provided in the drawings, wherein:

FIG. 1 is a schematic showing of a system in accordance with the invention;

FIG. 2 is an enlarged side elevation, partly broken away in cross-section, illustrating a chamber element of the system; and FIG. 3 is an enlarged perspective, illustrating the diffusing elements that are mounted on the inlet end of the chamber that is illustrated in FIG. 2.

DESCRIPTION OF THE PREFERRED EMBODIMENT

A procedure for filling a large vessel with inert gas in order to make it safe for working on the interior with open flame, etc., has heretofore involved the introduction of a relatively high pressure quantity of nitrogen. This was allowed to fill the vessel, and thereafter a check was made with a hand-held hydrogen detector in order to determine that the atmosphere in the vessel was safe. Since that procedure was subject to a false indication of safety because of possible formation of pockets of hydrogen or other explosive gas atmospheres, a better method was needed. It was discovered that by using a method or system according to this invention, the gas stream that was introduced could be monitored continously and so any hydrogen content detected and eliminated before it developed in any appreciable quantity in the vessel. A particular element of the invention is embodied by an adaptor that provides for the inline hydrogen detection in the case where the inerting gas is flowing under pressure, so that a sample may be diverted and the content thereof monitored for detection of any hydrogen therein.

With reference to FIG. 1, it may be noted that the system according to this invention is particularly applicable to operations where a substantial supply of an inert gas (such as nitrogen) is available under pressure, and also where there is a supply of compressed air similarly available. The procedure ordinarily employs a piping connection (not shown) that is made up in order to introduce a supply of nitrogen into one or more vessels (not shown) that are to be inerted, prior to doing work therein. It is during such inerting procedure that a system or method according to this invention is applicable. Thus, a nitrogen supply is provided through a pipe 11 as indicated in FIG. 1. It has the caption "Nitrogen Supply" applied thereto.

The nitrogen supply pipe 11 has a bleed connection 12 tapped off therefrom. It leads to a valve 15 which has a continuing connection 16 on the other side thereof that leads to a filter 17. This filter 17 is for removing any moisture in the gas flowing through the connection 16. The gas flow then continues through another connection 20 that goes to one end of a T connector 21. On the way, there is a branch connection 22 that goes to a pressure gauge 23. This part of the system provides for taking a representative sample of the nitrogen supply that is being monitored.

In the alternative, the gas stream to be monitored may be taken from a different source than the nitrogen supply line 11, e.g. the effluent from the vessel being purged. It will be understood that under these circumstances the valve 15 will be closed, and a connection 28 will be used. The connection line 28 connects from a vessel (not shown) which is being purged, and there is a valve 29 plus another connection 30 which joins the connection 16. The effluent gas flow then goes to the filter 17.

Of course, the nitrogen supply in pipe 11 would be under considerably more pressure than the effluent gas being displaced from the vessel which flows through the connection 28. However, any excess pressure is easily controlled by the adjustment of the valve 15. Thus, it would be expected that the valve 29 would be opened fully during monitoring of the effluent from a connected vessel or vessels. But, when the alternative monitoring of the nitrogen supply is being carried out, the valve 29 would, of course, be closed.

As indicated above, there is an air supply employed for being mixed with the inert gas that is being monitored. The purpose of such air supply will be more completely explained below. However, in the FIG. 1 diagram there is a situation indicated that usually exists in connection with a monitoring procedure according to this invention. The gas supply being monitored is high pressure nitrogen that is carried in a piping system 11 for introduction to a vessel or vessels being inerted. Adjacent to such nitrogen supply, there is a compressed air supply system that includes a compressed air pipe 33 which carries the compressed air therein, as indicated by the caption. A stream of air is bled from this compressed air source and carried through a connection 34 and a valve 35 to another connection 36 that leads to filter 39. This filter 39, like the filter 17 is for drying the gas which passes therethrough. From the other side of the filter 39 the dry air goes through a connection 40 that has a pressure gauge 41 connected thereto by another connection 42. The connection 40 leads directly to the other end of the T connector 21.

The common outlet of the T connector 21 has a connection 45 that leads to a valve 46 and from there via a connection 47, to the inlet of a chamber 50 where the mixture of nitrogen and dry air is monitored. The details of this chamber 50 will be described more fully below, but it will be observed in FIG. 1 that there is an outlet connection 51 at the other end of the chamber from the inlet 47. Also, there is a valve 52 and on the other side of valve 52 there is a curved vent pipe or connector 53. As employed in the system, the chamber 50 is mounted upright so that the gases going out the outlet end are carried through the vent connection 53 to the atmosphere via a semi-circle curve in order to prevent entry of any water in the vent.

FIGS. 2 and 3 illustrate in more detail the structural elements which make up the chamber 50 of this invention. The chamber 50 is made up of two pressed metal portions 57 and 58 that are joined by a collar 59. Each of these portions 57 and 58 of the chamber 50 has a necked down end 62 and 63 respectively. While the structure of the chamber 50 is symetrical, the arrangement is as illustrated which provides for the end 63 to be the inlet to the inside of the chamber and the other end 62 is the outlet end.

Associated with the inlet end 63 of the chamber 50 there is a means for diffusing the incoming mixture of dry air and nitrogen. Such means includes a pair of perforated thin discs 66 and 67. These act to diffuse the incoming gas mixture, and at the same time to cause any moisture in the gasses flowing through the perforations to be collected.

It may be noted that the disc 66 has a diameter that is slightly greater than the inside diameter of the pressed metal portion 58 so that when it is mounted therein it will create a tight contact with the walls of the chamber 50. Also, the disc 67 has a diameter slightly greater than the inside diameter of the inlet 63, so that when the discs are in place disc 67 will be in contact with the edges of the inlet 63.

It will be appreciated that the discs 66 and 67 will be mounted in the inlet portion of the chamber 50 before the joinder of the two portions 57 and 58. The mounting structure includes an axial spacer rod 70 from which the discs 66 and 67 extend transversely. The discs 66 and 67 are attached to the rod 70 in any feasible manner e.g. by being threaded thereon or otherwise having the location of each along the rod 70 fixed so as to have it act as a support as well as a spacer therebetween.

There is a hole (not shown) in the side of the chamber 50 which accomodates a hydrogen detector 74. Detector 74 is mounted transversely relative to the chamber 50 so that it extends into the interior and is subjected to the stream of mixed gases flowing thereover.

While various conventional detectors might be employed it is preferred to use one like the commercial gas monitor instrument that is available from Davis Instruments, 47 Halleck St. Newark, N.J. 07104. It is identified as a gas monitor model 11-3800A which employs a filament detector assembly model 11-3820N. That detector instrument includes structure which has a threaded hub or body 73 (shown in dashed lines) that may be received into a tapped hole (not specifically shown) mentioned above. Such hole is in the side of the portion 57 of the chamber 50, and so the detector 74 extends transversely across the mixed gas stream.

The detector is a hot wire type which employs an electrical bridge circuit. It has an output that provides a continuous signal for monitoring the pressure of any hydrogen. Such signal is indicated in FIG. 2 by a block 75 that carries the caption "monitor".

The detector 74 has active and reference filaments (not shown). The active filament is exposed to the mixed gas stream which is being monitored while the reference filament is enclosed in an air-tight cell. However, the active filament is surrounded by a flame arrestor 78 through which the gas stream may pass. The action involves maintaining the active filament at a certain temperature by adjusting the current through it, and then comparing conditions at the reference and active filaments. The variance between these two is proportional to the amount of hydrogen because whenever there is a combustible gas present there is a temperature rise on the active filament which causes a resistance change that is compared with the resistance of the reference filament. If the amount of hydrogen surrounding the active filament is sufficient to support combustion, the flame arrestor 78 will allow the combusted gas to pass through while blocking the flame front from entering the chamber 50. And, the chamber 50 is designed to withstand the pressure of the expanded gases, and to expel them to the atmosphere.

It will be understood that the valve 52 is connected in series with the vent pipe 53 and the connection 51 for use in shutting the vent passage when the adaptor is not in use. During use, the half-circle curve downward of the vent pipe 53 prevents entry of moisture.

While a particular embodiment of the invention has been described above in accordance with the applicable statutes, this is not to be taken as in any way limiting the invention but merely as being descriptive thereof.

We claim:

1. A system for monitoring an inert gas stream in order to detect hydrogen therein, comprising in combination
    a chamber for passing at least a portion of said gas stream therethrough and having an inlet and an outlet,
    said chamber inlet having a reduced cross sectional area relative to said chamber,
    means associated with said inlet for diffusing mixed gas streams and for collecting any moisture therefrom,
    said diffusing means comprising a pair of perforated diffusion plates mounted on a common support and extending transversely across said inlet and said chamber adjacent to said inlet,
    means for mounting a hydrogen detector in said chamber down stream from said diffusing means, and
    means for preventing moisture from entering said outlet.

2. A system according to claim 1, wherein said chamber is cylindrical.

3. An adaptor for in-line hydrogen detection comprising in combination, an elongated cylindrical chamber member having necked down ends thereon forming an inlet at one end and an outlet at the other,
    means for diffusing incoming gas at said inlet,
    said diffusing means comprising a pair of perforated thin discs extending transversely across said cylindrical chamber adjacent to said inlet end and across said inlet end respectively with spacer means for holding said discs in place,
    means for mounting a hydrogen detector in said chamber transversely thereof and downstream from said diffusing means, and
    means associated with said outlet for preventing entry of water therethrough.

4. An adaptor according to claim 3, wherein said outlet associated means comprises a vent pipe with a valve connected therein,
    said vent pipe being curved to aim its outlet downward when in use in order to prevent entry of water.

5. An adaptor for in line hydrogen detection comprising in combination, an elongated cylindrical chamber comprising two pressed metal portions joined by a collar,
    each of said portions having a necked down end,
    one of said ends forming an inlet and the other forming an outlet of said chamber,
    means for diffusing incoming gas at said inlet comprising
    a pair of perforated thin discs attached to an axial spacer rod and extending transversely thereof,
    one of said discs having a diameter slightly greater than the inside diameter of said pressed metal portions,
    the other of said discs having a diameter slightly greater than the inside diameter of said inlet,
    said discs and spacer rod being adapted for mounting in said inlet portion of said chamber prior to joinder of said outlet portion with said collar,
    a hole in the side of said outlet portion of said chamber adapted for mounting a hydrogen detector transversely in said chamber, and
    means associated with said outlet for preventing entry of water therethrough comprising
    a vent pipe connected to said outlet having a valve connected therein for shutting said vent when the adaptor is not being used for hydrogen detection, and
    said vent pipe ending in a half circle curve downward when the adaptor is in use in order to keep said water out.

* * * * *